United States Patent
Moddemeyer et al.

(10) Patent No.: US 7,880,875 B2
(45) Date of Patent: Feb. 1, 2011

(54) APPARATUS AND METHOD FOR INSPECTING CIRCUIT STRUCTURES

(75) Inventors: Kees Moddemeyer, Leiden (NL); Henri Johannes Petrus Vink, The Hague (NL); Pieter Willem Herman de Jager, Rotterdam (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 74 days.

(21) Appl. No.: 12/280,922

(22) PCT Filed: Feb. 28, 2007

(86) PCT No.: PCT/NL2007/050079

§ 371 (c)(1), (2), (4) Date: May 19, 2009

(87) PCT Pub. No.: WO2007/100249

PCT Pub. Date: Sep. 7, 2007

(65) Prior Publication Data

US 2009/0219519 A1    Sep. 3, 2009

(30) Foreign Application Priority Data

Feb. 28, 2006 (EP) .................... 06075459

(51) Int. Cl.
*G01N 21/00* (2006.01)
(52) U.S. Cl. .................. 356/237.2; 356/237.5
(58) Field of Classification Search .......... 356/237.2, 356/237.5
See application file for complete search history.

(56) References Cited

U.S. PATENT DOCUMENTS

| | | | | |
|---|---|---|---|---|
| 5,369,481 A * | 11/1994 | Berg et al. | ............... | 356/319 |
| 5,535,006 A * | 7/1996 | Telschow et al. | ............ | 356/394 |
| 5,598,008 A * | 1/1997 | Livoni | ................... | 250/586 |
| 6,180,955 B1 * | 1/2001 | Doggett et al. | .......... | 250/586 |
| 7,508,504 B2 * | 3/2009 | Jin et al. | ................ | 356/237.4 |
| 2003/0202180 A1 | 10/2003 | Gobel et al. | | |
| 2004/0001344 A1 | 1/2004 | Hecht | | |

FOREIGN PATENT DOCUMENTS

EP      1 043 580 A2     10/2000

OTHER PUBLICATIONS

International Search Report for PCT/NL2007/050079 dated May 22, 2007.

* cited by examiner

*Primary Examiner*—Roy Punnoose
(74) *Attorney, Agent, or Firm*—Leydig, Voit & Mayer, Ltd.

(57) ABSTRACT

An apparatus is described for scanning a circuit structure. The apparatus has a linear sensor (16) for detecting light intensity as a function of position along the sensor. A transport mechanism (12) moves a circuit structure (10), such as a PCB or a wafer relative to the sensor. The circuit structure is illuminated with an illumination system (14) that comprises a hollow cylinder (144) with a mainly diffusively and/or specularly reflecting inner wall surface. The cylinder is arranged in parallel with the sensor and has a first slit (40) and a second slit (42) located so that a virtual plane runs through the sensor, the first and second slit to a location for the circuit structure under inspection. The illumination system furthermore comprises a linear light source (146) in the cylinder or the inner wall of the cylinder. In an embodiment the illumination system comprises a splitting mirror (22) in the cylinder to reflect light to the circuit structure.

30 Claims, 4 Drawing Sheets

APPARATUS AND METHOD FOR INSPECTING CIRCUIT STRUCTURES

FIELD OF THE INVENTION

The invention relates to a circuit structure inspection apparatus, such as a PCB (Printed Circuit Board) inspection apparatus or a wafer inspection apparatus.

BACKGROUND

It is known to perform inspection of a printed circuit boards by optical scanning of the printed circuit board. In view of the high resolution required for reliable inspection, typically an image of one or a few lines along the circuit board at a time is captured with a line sensor. The printed circuit board and the line sensor are moved relative to one another in a scanning direction transverse to the linear direction of the sensor. Thus an image of the printed circuit board is progressively scanned.

One important aspect of the design of such an inspection apparatus is the illumination system. High demands are placed on this illumination system. It must provide light of high intensity on the line on the printed circuit board that is being scanned. At the same time, this light should be such that oblique surface parts of the printed circuit board, for example near the edges of conductor track will not lead to inspection errors.

U.S. Pat. Nos. 4,877,326 and 5,058,982 disclose illumination systems for PCB inspection that use a central linear light source configured to illuminate a line on a substrate from the direction of the sensor. In addition auxiliary linear light sources are provided on either side of the central linear light source. Curved mirrors are provided to image the auxiliary light sources onto the substrate, so that light from each auxiliary light source arrives from a range of directions along the line on the substrate.

From the different art of document scanning, it is known from U.S. Pat. No. 5,825,945 to illuminate a document by means of a Lambertian cylinder, that is, a cylinder with diffusively (not specularly) reflective inner walls. A light source is provided in the cylinder. The cylinder has a slit that passes light from the interior of the cylinder to a line on the document where the document is scanned.

SUMMARY OF THE INVENTION

Among others it is an object of the invention to provide for a PCB inspection apparatus with an illumination system that is robust in design.

A printed circuit board scanner apparatus is according to claim 1 is provided. Herein an illumination system is used that comprises a hollow cylinder with a diffusively and/or specularly reflective inner wall surface. The cylinder has a first slit and a second slit extending along the sensor direction located so that a viewing line (plane) runs through the first and second slit to a location for the printed circuit board under inspection. The illumination system furthermore comprises an internal linear light source in the cylinder or the inner wall of the cylinder. In this way lighting of the PCB from a range of directions is ensured. The linear light source may be in one part, or constructed from a series of light source elements.

In an embodiment a cylinder with a semi-circular cross-section is used, a flat part of the semi-circular cross-section facing the substrate. However, cylinders with differently shaped cross-section may be used.

In further embodiments the cylinder comprises a splitting mirror in or at the edge of the cylinder at an angle to the printed circuit board, to reflect light from inside the cylinder towards the printed circuit board from a direction of the second slit. Thus, no additional light source is needed when lighting from a viewing direction is also required.

In another embodiment the angle of the splitting mirror is so that the splitting mirror reflects light to the first slit from a surface part of the cylinder that is lighted directly by the light source. This ensures strong lighting from the viewing direction.

In another embodiment at least two light sources are used in the cylinder on mutually opposite sides of the virtual plane. This improves the distribution of light over a range of angles. In a further embodiment an intensity control circuit provided to adapt a relative intensity of the light sources for different printed circuit boards.

In another embodiment time delayed integration is used. In this embodiment the lighting system ensures that comparable lighting conditions are provided for successive locations for time delayed integration.

BRIEF DESCRIPTION OF THE DRAWINGS

These and other objects and advantageous aspects will become apparent from the description of exemplary embodiments, using the following figures.

DETAILED DESCRIPTION OF THE DRAWINGS

Figure 1:
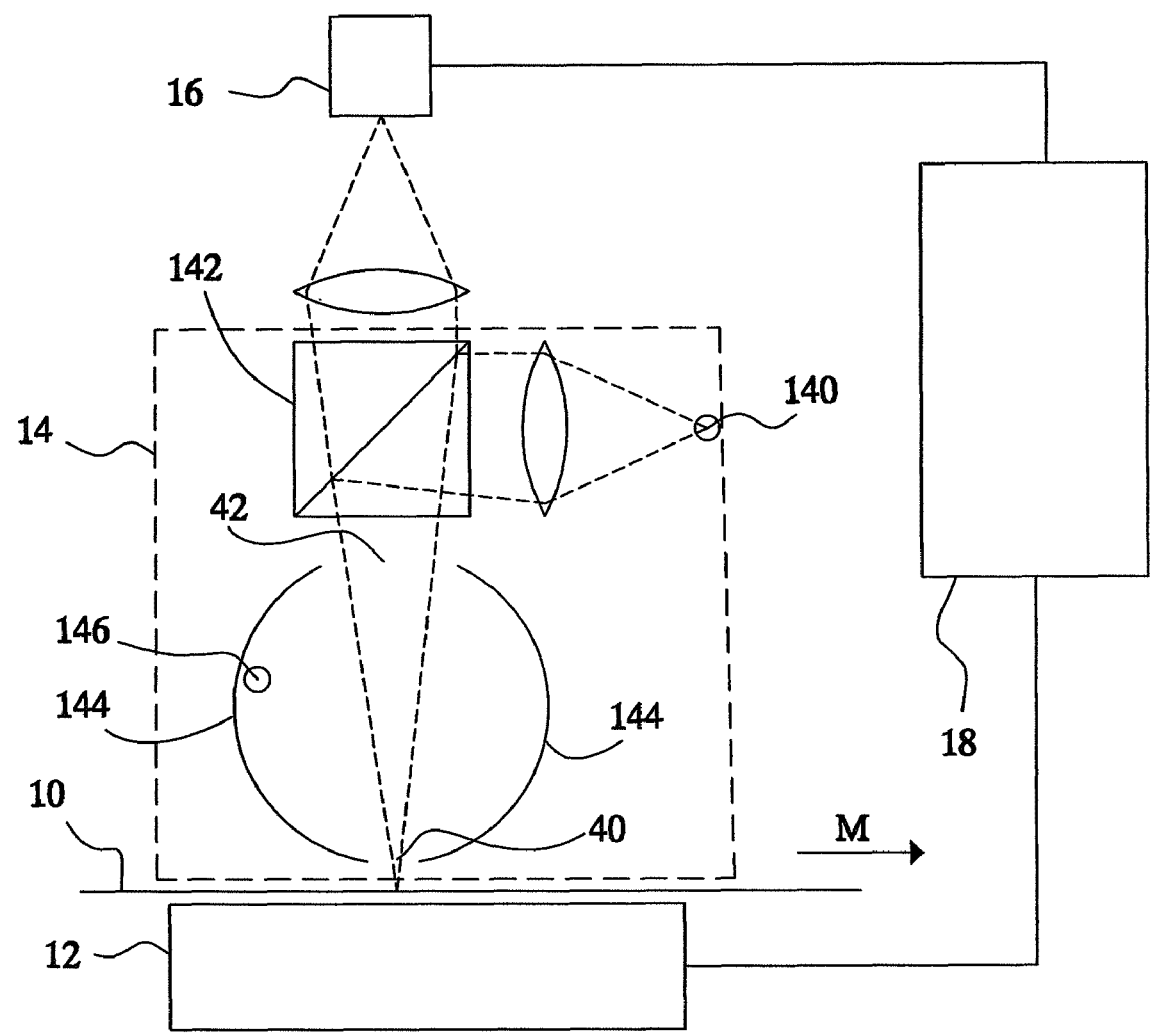
FIG. 1 shows a PCB inspection apparatus

FIG. 1 shows a PCB inspection apparatus. The apparatus is shown in combination with a PCB 10 (Printed Circuit Board) under inspection. The apparatus contains a transport system 12, an illumination system 14, a sensor 16 and a data processing system 18. PCB 10 is supported by transport system 12. Sensor 16 is a linear sensor, which extends in a sensor direction that is perpendicular to the plane of the drawing (or more generally at a non-zero angle transverse to that plane). Sensor 16 and transport system 12 are coupled to data processing system 18.

Illumination system 14 comprises a linear light source 140, a combiner 142, a hollow cylinder 144 and an internal linear light source 146. Linear light source 140, combiner 142, cylinder 144 and internal linear light source 146 all extend in parallel with sensor 16 along the sensor direction. Hollow cylinder 144 has a diffusively reflective inner wall surface. That is, the returned light, which is returned by the inner wall surface when light impinges on a point of the inner wall surface from a given angle of incidence, is returned as returned light over a range of angles (preferably at least ninety degrees), possibly with an angle dependent intensity distribution, but without specular reflection (reflection in one direction dependent on the angle of incidence of the light at the point), or at least without substantial specular reflection (i.e. less than fifty percent and preferably less than ten percent or more preferably less than one percent specular reflection). The diffusive and/or specular reflectivity of the inner wall surface is high, preferably at least ninety percent and more preferably at least ninety eight percent. Techniques for producing such wall surfaces are known per se. The inner wall surface, or its reflective part, may be entirely diffusively or entirely specularly reflective, or part may be diffusively reflective and another part may be specularly reflective.

A first and second slit 40, 42 are provided in the wall of cylinder 144. The slits 40, 42 extend in the sensor direction in parallel with sensor 16. The first slit 40 faces PCB 10, so as to allow light from the cylinder to pass to PCB 10. The second slit 42 faces combiner 142 and sensor 16 and placed in relation to the first slit 40, so that light from combiner passes to PCB 10 through the second and first slit 42, 40 successively and reflected light from PCB 10 passes to sensor 16 via the first and second slit successively. Preferably, the first slit is substantially as large as necessary to allow PCB 10 to be imaged onto sensor 16, without imaging the inner wall of cylinder 144 onto sensor 16 in such a way that light from the inner wall directly affects sensor output. In an embodiment the slits are at least ten centimeter long, for example twenty centimeter. In an embodiment the slits are at most one centimeter wide, for example seven millimeter.

In operation transport system 12 moves PCB 10 along a scanning direction (shown as an arrow M) transverse to the sensor direction. Although a transport system is shown that transports PCB 10 relative to illumination system 14 and sensor 16, it should be understood that alternatively a transport system may be used that transports illumination system 14 and sensor 16 relative to PCB 10, or provides a combination of both forms of transport.

Illumination system 14 provides a line of light on PCB 10. Part of the light is provided by light source 140, which is focussed onto the line on PCB 10 and reflected into the line of sight of sensor 16 by combiner 142. Another part of the light on the line on PCB 10 is produced by reflection light from the inner wall of cylinder 144. Light from internal linear light source 146 reflects from to inner wall and reflects back onto different wall portions any number of times until it leaves cylinder 144 through the first slit 40 to reach PCB 10. Because of the internal reflections in cylinder 144, the intensity of the light that reaches PCB 10 has no "blind angles of incidence" from which there is little or no intensity. As a result, it is ensured oblique surfaces at arbitrary angles on PCB 10 will reflect light to sensor 16.

The line on PCB 10 is imaged onto sensor 16. Sensor 16 converts the received light intensity as a function of position along the sensor direction into electronic signals and feeds these electronic signals to data processing system 18. Data processing system 18 associates the electronic signals with positions on the PCB that are assumed during scanning (for example by controlling transport system 12 to assume successive positions, or by receiving back information about measured positions from transport system 12). Data processing system then uses the electronic signals to produce inspection result signals, and or error indication signals for the PCB 10 under inspection. Techniques for this are known per se.

Figure 2:
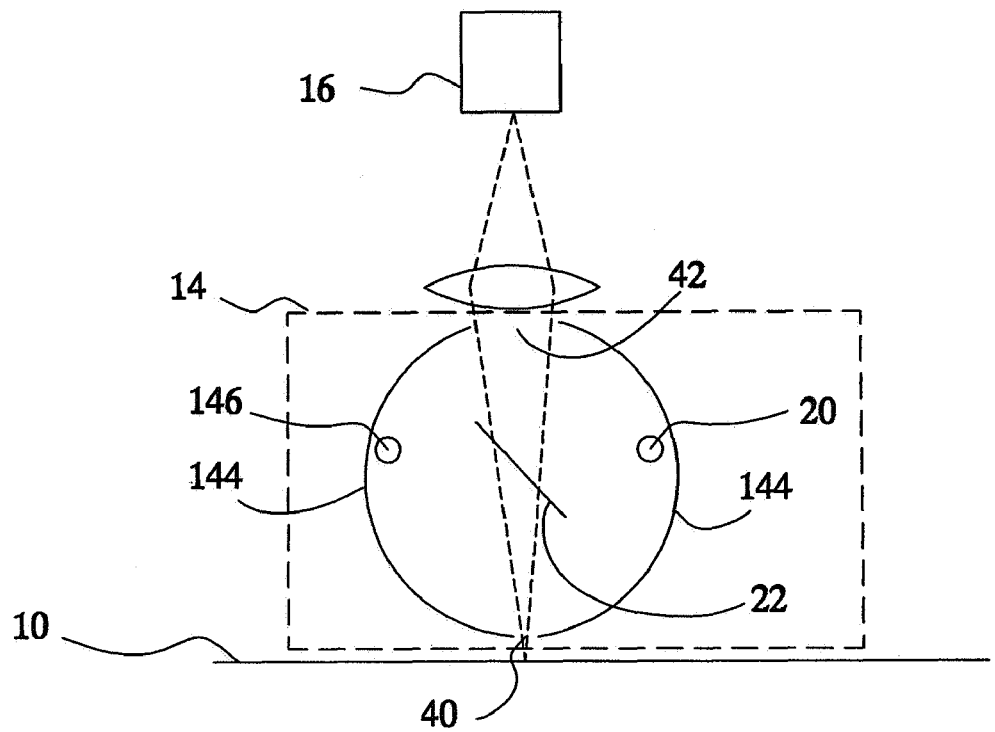
FIG. 2 shows a cross-section of an illumination system

FIG. 2 illustrates an alternative illumination system 14. Herein a splitter mirror 22 is provided inside cylinder 144. Furthermore an optional second internal linear light source 20 has been provided in cylinder 144. In this embodiment no external light source for supplying light through the slits 40, 42 in cylinder 144 to PCB 10 is present. This has the effect that no light from the direction of the second slit 42 (from the side of the sensor (not show) reaches PCB 10 through the first slit 40. Splitter mirror 22 has been included to reflect part of the internally reflected light in cylinder 144 towards the first slit 40 along a direction that runs from the second slit 42 to the first slit 40. This makes up for the absence of light that comes in through the second slit 42.

Splitter mirror 22 reflects only a fraction of the light that impinges on splitter mirror. Splitter mirror 22 transmits a majority of the light. Thus a significant amount of internal reflection will typically occur before the light leaves cylinder 144. Splitter mirror 22 is shown only schematically. In practice a smaller or larger splitter mirror or a curved splitter mirror may be used, as long as the amount of light reflected towards the first slit 40 along directions from the second slit 42 toward the first slit 40 is comparable to the amount of light reflected to the first slit 40 by the inner wall surface of cylinder 144 from other directions. Preferably, splitter mirror 22 and internal light sources 146, 20 are located so that no light directly from the internal light sources 146, 20 is reflected towards the first slit 40 (or so that such directly reflected light is reflected along a broad range of angles relative to the PCB surface).

Figure 3:
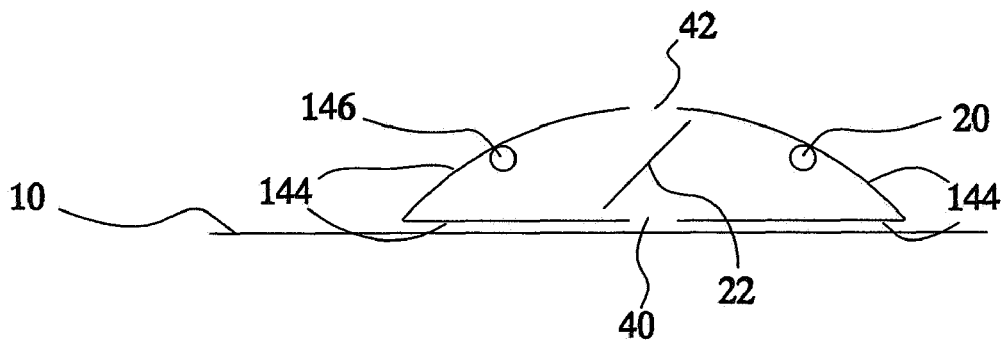
FIGS. 3-5 shows cross-sections of a part of an illumination system

FIG. 3 shows a cross-section of an alternative illumination system. Herein a cylinder is used with a non-circular cross section. Inner surface parts of cylinder 144 on a side of cylinder 144 away from PCB 10 are provided at a non-zero angle to PCB (in the example at a plurality of such angles because these surface parts are curved). This type of illumination system has the advantage that it is more compact, while it still realizes illumination from a range of angles. The later is ensured by the fact that the inner wall parts of the cylinder are located at an angle with respect to each other, so that most light reflects back and forth between the walls a plurality of time before passing out to the PCB through the first slit 40.

Although light sources 146, 20 inside cylinder 144 have been shown, it should be appreciated that alternatively light sources may be used that are part of inner wall of the cylinder 144.

In one embodiment a sensor 16 with a single row of sensing elements along the sensor direction is used. Such a sensor can be used to scan the entire PCB when the PCB is moved relative to the sensor.

In another embodiment Time Delay and Integration (TDI) is used. In this embodiment a sensor with a plurality of rows of sensing elements is used, successive rows having mutually adjacent positions along the transport direction. In this embodiment data processing system integrates (or sums) measurements I (x, n, t) from sensing elements in successive rows (labelled n=0,1, ... ) at corresponding positions x in the sensor direction.

Data processing system 18 combines measurements for different time points I (x,n,t-n*d/v) from different rows n in each sum to produce respective summed output signals S (x, t) for different positions x along the sensor direction and a time points t (d being the distance between successive rows and v being the apparent velocity of motion of PCB 10, as visible at the sensor 16). These parameters are selected so that the summed measurements I (x,n,t-n*d/v) from different rows n, correspond to images of the same location on PCB 10 at different time points as it moves along the transport direction. The sum S (x,t) is representative of a reflection property of PCB 10 at a position x, y where y is proportional to t/v.

TDI increases the signal to noise ratio to compensate effect of high speed of motion. A relatively low light intensity can be used, which prevents undue heating of cylinder 144. When TDI is used the width of the slits 40, 42 is preferably chosen so that each on of the rows of sensor a part of the PCB is imaged, with direct effect of imaging of the inner wall of cylinder 144.

In a further embodiment a pulsed illumination source or sources 20, 146 are used. This reduces heat production. Preferably, the apparatus is configured to activate the pulses in synchronism with movement during TDI. This reduces requirements on motion accuracy.

Figure 4:
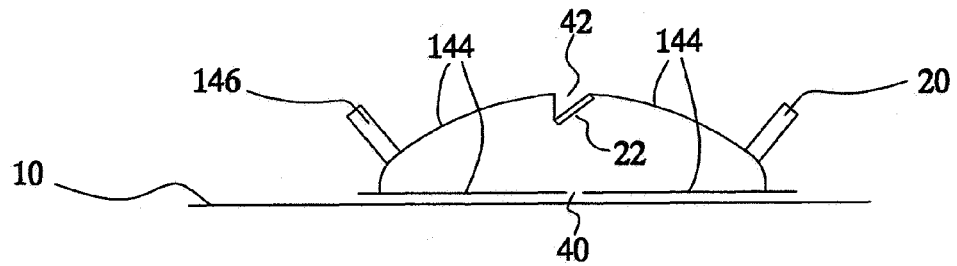

FIG. 4 shows a cross-section of another alternative illumination system with a cylinder with a non-circular cross section. Inner surface parts of cylinder 144 on a side of cylinder 144 away from PCB 10 are provided at a non-zero angle to PCB (in the example at a plurality of such angles because these surface parts are curved). Splitter mirror 22 is mounted on a baffle fitting, which closes off the opening of the cylinder towards the sensor 16 (not shown), except through splitter mirror 22. This prevents that stray light is transmitted from the cylinder to the sensor.

Figure 5:
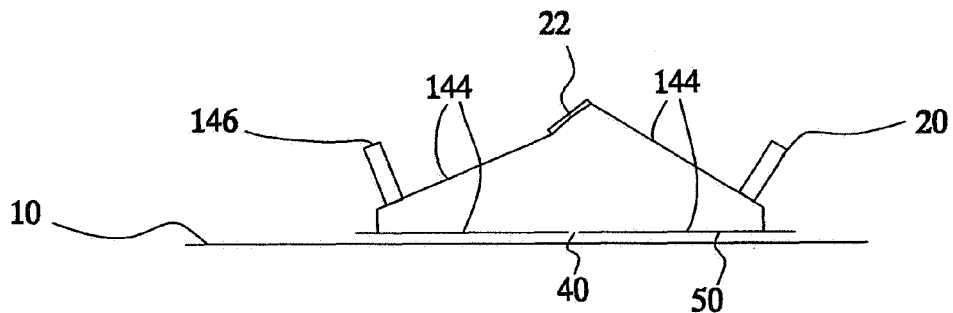

FIG. 5 shows a cross-section of another alternative illumination system with a cylinder with planar surfaces. Inner planar surface parts of cylinder 144 on a side of cylinder 144 away from PCB 10 are provided at a non-zero angle to PCB. Splitter mirror 22 is mounted between the edges of parts of cylinder 144 on the left and right of the second slit 42 (left and right in the figure with respect to line (plane) of view through the cylinder from the sensor to the PCB). Thus, light is reflected towards the PCB from the direction of the second slit 42 without creating dead angles inside cylinder 144.

Preferably, splitter mirror 22 is mounted at an angle so that it reflects light from a surface part 50 of cylinder 144 on the side of cylinder next to the PCB to first slit 40. More preferably splitter mirror 22 is mounted at an angle so that this surface part 50 is lighted directly by the light source 20. This makes it possible to control the intensity of light that is projected on to the PCB from the viewing direction by controlling the intensity of the relevant light source 20. In an embodiment the apparatus comprises a light intensity control circuit, configured to control the intensity of the different light sources 20, 146 in the cylinder 144 relative to one another. Thus, the ratio of the light intensity of light projected onto the PCB from the viewing direction on one hand and light from other directions on the other hand can be controlled and set independently for inspection of different types of PCB.

More preferably splitter mirror 22 is mounted at an angle so that light directly from light source 20 that reflects in a specular reflection direction (angle of incidence equals angle of emergence) from the surface part 50 to splitter mirror 22 is reflected by splitter mirror 22 to first slit 40.

In an embodiment, wall surface of cylinder 144 is prepared so that there are relative differences in diffusive and/or specular reflectivity between a surface part that contains a point located to reflect light directly from light source 20 directly to slitter mirror 22 under specular reflection conditions (angle of incidence equals angle of emergence) and a remainder of the surface of the inner wall. The surface is preferably prepared to have a higher (diffusive and/or specular) reflectivity in said surface part than in the remainder. This makes it easier to control over the distribution of light from different directions. Preferably, at least the relevant surface part on the side of the cylinder that provides light that is reflected by splitter mirror 22 to first slit 40 is prepared in this way.

In an embodiment wall surface of cylinder 144 is prepared so that it has anisotropic reflection properties, reflecting light rays predominantly specularly when the rays are in a plane perpendicular to the surface along a first direction of the surface (called the x-direction) and reflecting rays predominantly diffusively when the rays are in a plane perpendicular to the surface along a second direction of the surface (called the y-direction) perpendicular to the first direction. This can be realized for example by rubbing the surface moving sandpaper along the x-direction. In an embodiment the first direction is made parallel to the sensor direction. In this way the light through first slit can be given a selected distribution of angles of incidence in a plane through the slit, of angles between for example minus and plus forty five degrees or between minus and plus sixty degrees, not wider. The distribution of angles in a plane perpendicular to the slit, on the other hand can be controlled using the distribution of the light source and the form of the cylinder to counteract illumination artefacts. It should be appreciated that part or all of the wall surface may be treated in this way.

Preferably, the surface of splitter mirror 22 is curved so that if reflects light from a range of directions is reflected through first slit 40. Preferably the curvature is selected so that light from the before mentioned surface part 50 is reflected to first slit 40 over all directions that correspond to the direction to second slit 42.

It may be noted that the mounting of splitter mirror 22 between the edges of parts of cylinder 144 at an angle to the viewing direction through the first and second slits 40, 42 implies that the distances of these edges to the PCB differ. This may be realized by using walls of cylinder 144 at mutually different angles with respect to the PCB on the left and right. Alternatively the left and right parts of cylinder 144 may have different widths.

Light source 20, 146 may be of any type. For example a laser light source may be used, a fluorescent tube etc. In an embodiment, an array of LEDs (semi-conductor Light Emitting Devices) is used. In a further embodiment the LEDs in the array comprise LEDs of a plurality (e.g. two) mutually different types.

Figure 6:
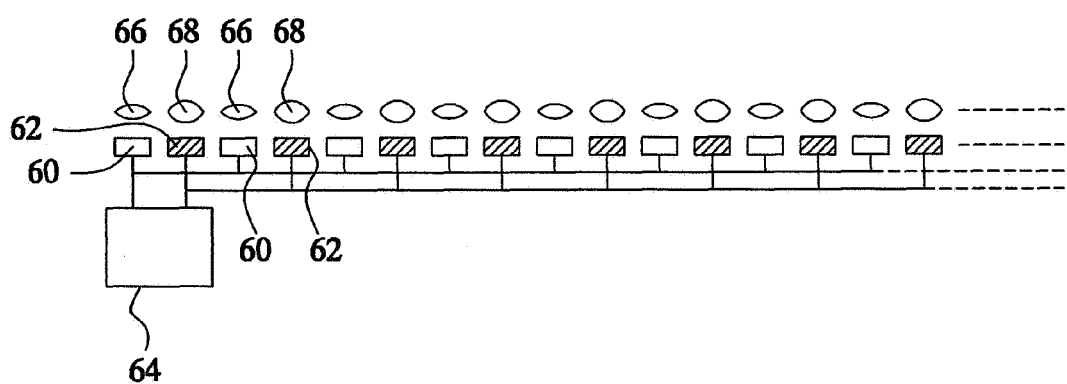
FIG. 6 shows a light source

FIG. 6 shows an array of LEDs 60, 62 (only some indicated explicitly), a driver circuit 64 and lenses 66, 68 (only some indicated explicitly). LEDs 60, 62 of alternating type are provided successively (different types indicated by shading). The term "type" as used herein applied to LEDs refers to the functional effect of the configuration in which the LED is used as well as the type of LED chip proper. Thus, if the functional effect of the configuration on the optical properties of light supplied to the interior of cylinder 144 is different the LEDs are said to be of different type, even if the chips are the same. Lenses 66, 68 are part of the LED configuration of the LED in this sense. Lenses 66, 68 of a first and second type (for example with different focal lengths) are provided for projecting light into cylinder 144 (not shown).

As shown in the figure LEDs 60, 62 of different type are shown arranged in series, alternately along the sensor direction. In an alternative embodiment, the LEDs may be arranged in rows, each row containing LEDs of different types arranged in series in a direction transverse to the sensor direction, the rows being arranged in parallel with one another successively along the sensor direction. In each case LEDs 60, 62 of a specific type form a sub-array of the array of LEDs for each type, the sub-arrays extending along the sensor directions.

Driver circuit 64 has separate drive outputs for LEDs 60 of the first type and LEDs 62 of the second type. Driver circuit 64 is configured so that a relative drive strength of LEDs of the different types. In this way the focus properties of the light source can be adapted by changing the driving strengths. It should be appreciated that although an embodiment with parallel driving is shown, this can also be realized if the driving circuit may of course have separate outputs for individual LEDs 60, 62 or groups of LEDs. Furthermore, it should be appreciated that although an example with two types of LEDs is shown, any greater number of types may be used, so that the drive strengths of LEDs of the different types can be adjusted. This provides greater control over lighting properties.

Furthermore, although an example has been shown wherein different lenses 66, 68 are used for different types of LEDs 60, 62, it should be appreciated that alternatively other properties of the LEDs (such as spectral properties and radiation angle) of the LEDs may also be different or that the lenses 66, 68 for the different types may be the same, or that one or even both types may not have a lenses.

In a further embodiment filters (not shown) with wavelength and/or polarization dependent absorption properties may be inserted between the LEDs 60, 62 and the interior of cylinder 144. In an embodiment the apparatus may be arranged to provide for exchange of the filters, in order to adjust lighting properties. Also different types of filters may be used for different types of LEDs (or to make the type of LED functionally different). In this way the driving strength of the LEDs can be used to change the filtering effect. Alternatively, or in addition, the apparatus may be configured to provide for an exchangeable filter (not shown) between second slit 41 and sensor 16.

In another embodiment optical fibres (not shown) that act as light guides are inserted between the LEDs 60, 62 and the interior of cylinder 144. In this way heat production inside the cylinder can be reduced. The fibers may be between the lenses and the LEDs proper to provide controlled lighting, or between the lenses and the cylinder, or with lenses on both sides of the fiber or on neither side.

In addition to, or instead of, control of lighting properties by the relative drive strength of the LEDs 60, 62 lighting properties may also be controlled by the absolute drive strength of the LEDs, even in an embodiment wherein only one type of LED is present.

Figure 7:
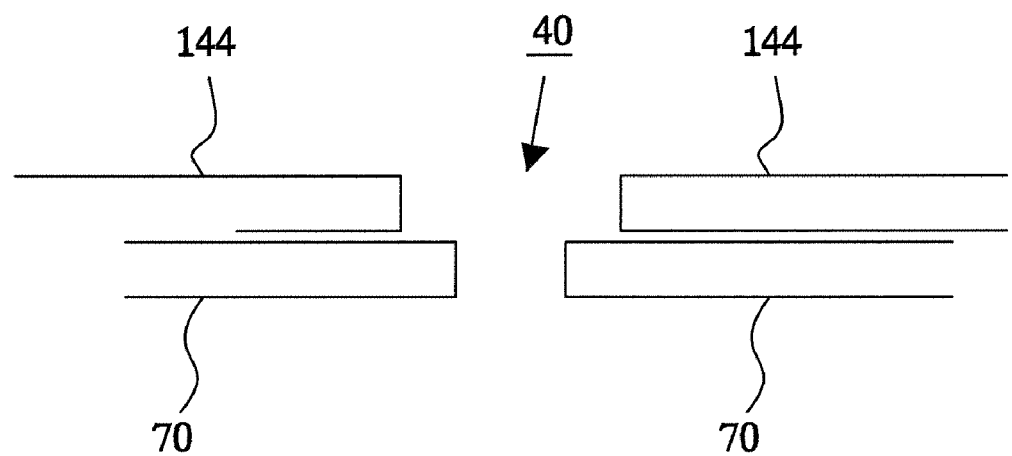
FIG. 7 shows a detail of a slit
FIG. 8 show a cross-section of a part of an illumination system

FIG. 7 shows a detail of an embodiment wherein a linear diaphragm 70 is provided adjacent first slit 40. Respective parts of the diaphragm 70 on the left and right of first slit 40 are mounted movably relative to one another. Thus, the width of first slit 40 can be adapted. In this way the angular illumination characteristic can be adapted.

Figure 8:
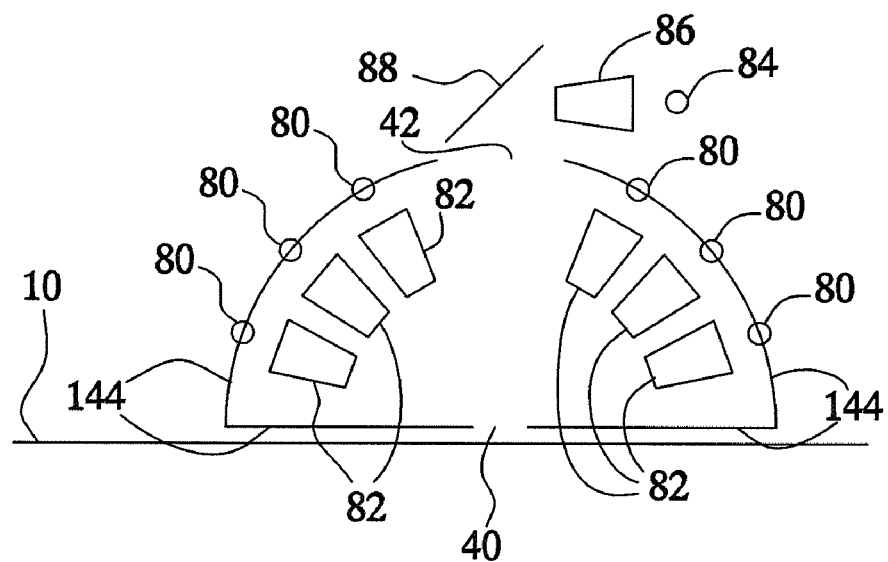

FIG. 8 illustrates a cross-section of an alternative illumination system 14. Herein a plurality of linear light sources 80 is provided on the wall of cylinder 144 (shown in cross-section transverse to the linear extension of the light sources). Light concentrators 82 are provided in cylinder 144, between respective ones of light sources 80 and slit 40. An additional light source 84 and corresponding concentrator 86 are provided outside cylinder 144. A splitter mirror 88 is provided outside cylinder, configured to redirect light received through the corresponding concentrator 86 from additional light source 84 to slit 144. splitter mirror 22 is provided inside cylinder 144.

Light concentrators 82 are configured to concentrate light from respective light sources 80 in the direction towards slit 40. For this purpose, light concentrators deflect (change the direction of radiation of) respective parts of the light from the corresponding light source relative to one another, whereby a part of the light that is not radiated towards slit 40 is redirected to slit 40. This increases light intensity at slit 40. Light concentrator 82 may comprise a lens to concentrate the light (no imaging of the light source onto the slit is required). Alternatively or in addition, light concentrators 82 may comprise diffusively and/or specularly reflecting surfaces configured to reflect part of the light that is emitted from a light source 80 directed away from the direction of slit 40 into a direction of slit 40. An angle is left open between the light sources 80 and concentrators 82 for a slit 42 through which the PCB can be observed via slit 40. Use of concentrators 82 has the advantage that a higher light intensity can be realized at slit 40.

Additional light source 84 is used to supply light from the direction from which the PCB is observed. Light from additional light source 84 is concentrated in the direction of slit 40 by additional concentrator 86 in a similar way the light from the other light sources. Use of additional light source 84 and corresponding concentrator 86 has the advantage that a higher light intensity can be realized at slit 40 from the direction from which the PCB is observed. Preferably, the angle left between light sources 80 and concentrators 82 is equal to the angle used for one of the light sources 80 with its concentrator 82. In this case a single additional light source 84 and corresponding concentrator 86 may be used. When a larger angle is used, a proportionally larger number of additional light sources 84 and/or corresponding concentrators 86 may be used outside cylinder 144.

As will be appreciated the various means for adapting the illumination properties are provided so that the illumination properties can be adapted during use of the apparatus, for example to adapt to different types of product, or to counteract problems that have arisen during inspection of a batch of products.

The invention claimed is:

1. A circuit structure scanner apparatus,
a sensor extending along a sensor direction, for detecting light intensity as a function of position along the sensor direction;
a transport mechanism configured to move a circuit structure under inspection and the sensor relative to one another in a transport direction transverse to the sensor direction;
an illumination system, comprising a hollow cylinder with a mainly diffusively and/or specularly reflecting inner wall surface, arranged in parallel with the sensor extending along the sensor direction, the cylinder having a first slit and a second slit extending along the sensor direction located so that a virtual plane, which goes through the sensor in parallel with the sensor direction, runs through the first and second slit to a location for the circuit structure under inspection, the illumination system furthermore comprising an internal linear light source in the cylinder or the inner wall of the cylinder, extending along the sensor direction.

2. A circuit structure scanner apparatus according to claim 1, further comprising a splitting mirror located between edges of the cylinder that are adjacent to the second slit, the splitter mirror extending in the sensor direction, at an angle to the circuit structure to reflect light from inside the cylinder towards the circuit structure from a direction of the second slit.

3. A circuit structure scanner apparatus according to claim 2, wherein the angle to the circuit structure of the splitting mirror is such that the splitting mirror reflects light to the first slit from a surface part of the cylinder that is lighted directly by the light source.

4. A circuit structure scanner apparatus according to claim 3, wherein the angle to the circuit structure of the splitting mirror is such that an angle of incidence from the light source to said surface equals an angle of emergence from said surface part to the splitting mirror.

5. A circuit structure scanner apparatus according to claim 3, wherein a reflecting surface of the splitting mirror is curved, with a curvature so that light from said surface part is reflected to the first slit over a range of angles that corresponds to a width of the second slit.

6. A circuit structure scanner apparatus according to claim 1, further comprising a splitting mirror located within the hollow cylinder and extending in the sensor direction, the splitting mirror being located to reflect light from the inner wall surface through the first slit along a direction in said virtual plane.

7. A circuit structure scanner apparatus according to claim 6, wherein the splitting mirror is mounted on an optical baffle, located to close a gap between an edge of the splitting mirror and an edge of the second slit along the sensor direction, whereby light leaking from the cylinder to the sensor is blocked.

8. A circuit structure scanner apparatus according to claim 1, wherein the light source is located in a first part of the cylinder or the inner wall of the cylinder, the scanner apparatus comprising a further internal linear light source in a second part of the cylinder or the inner wall of the cylinder, the first and second part being on mutually opposite sides of the virtual plane.

9. A circuit structure scanner apparatus according to claim 8, comprising an intensity control circuit configured to adapt a relative intensity of the light source and the further light source.

10. A circuit structure scanner apparatus according to claim 1, wherein the sensor comprises a plurality of adjacent rows of sensing elements, each row extending along the sensor direction, the apparatus furthermore comprising a data processing system, configured to perform time delay and integration of signals from sensing elements in respective ones of the rows.

11. A circuit structure scanner apparatus according to claim 2, wherein reflective and/or diffusive properties of the inner wall are position dependent, and an inner wall region, which contains a point from which virtual lines at equal angles to the inner wall at that point run to the splitting mirror and the light source, having a higher reflectivity than a remainder of the inner wall.

12. A circuit structure scanner apparatus according to claim 1, wherein the linear light source comprises an array of light emitting diodes.

13. A circuit structure scanner apparatus according to claim 12, further comprising light guides inserted between respective ones of the light emitting diodes and the interior of the hollow cylinder.

14. A circuit structure scanner apparatus according to claim 12, wherein the light emitting diodes are provided in configurations that enable tuning of one or more of the following set of parameters including: emission wavelength, range of radiation angles, and focus position of emitted light.

15. A circuit structure scanner apparatus according to claim 1, wherein a plurality of arrays of light emitting diodes of respective types are included in the linear light source, the scanner apparatus further comprising a driving circuit coupled to the light emitting diodes in the respective arrays, the driving circuit being configured to provide for adjustment of relative drive strengths of the light emitting diodes in the respective arrays.

16. A circuit structure scanner apparatus according to claim 1, wherein at least part of the inner wall of the hollow cylinder has anosotropic reflection properties, providing a varying ratio between diffusive and specular reflection dependent on an angle of incidence of light on said part of the inner wall.

17. A circuit structure scanner apparatus according to claim 1, further comprising an adjustable linear diaphragm adjacent the first slit.

18. A circuit structure scanner apparatus according to claim 1, further comprising a spectral filter between the linear light source and the hollow cylinder and/or between the hollow cylinder and the sensor.

19. A circuit structure scanner apparatus according to claim 1, wherein the light source comprises a laser.

20. A circuit structure scanner apparatus according to claim 1, wherein the linear light source is a pulsed linear light source.

21. A circuit structure scanner apparatus according claim 20, wherein a timing of light pulses from the pulsed linear light source is synchronized to movement of the substrate.

22. A circuit structure scanner apparatus according to claim 1, wherein at least part of the inner wall surface wall has anistropic reflection properties.

23. A circuit structure scanner apparatus according to claim 1, comprising a plurality of light sources on the walls of the cylinder or within the cylinder and respective light concentrators, each light concentrator being positioned relative to a respective one of the light sources to concentrate light from the respective one of the light sources towards the first slit.

24. A circuit structure scanner apparatus according claim 23, further comprising an additional light source outside the cylinder, a splitter mirror outside the mirror directed to reflect light from the additional light source towards the first slit and an additional concentrator located between the additional light source and the splitter mirror, positioned to concentrate light from the additional light source towards the first slit.

25. A method of inspecting a circuit structure, the method comprising:
  moving the circuit structure and a scanner relative to each other in a transport direction;
  sensing light returned from the circuit structure using a sensor extending along a sensor direction transverse to the transport direction;
  lighting the circuit structure using a hollow cylinder with a mainly diffusively and/or specularly reflecting inner wall surface, arranged an parallel with the sensor extending along the sensor direction, the cylinder having a first slit and a second slit extending along the sensor direction located so that a virtual plane, which goes through the sensor in parallel with the sensor direction, runs through the first and second slit to a location for the circuit structure under inspection, the illumination system furthermore comprising an internal linear light source in the cylinder or the inner wall of the cylinder, extending along the sensor direction.

26. A method according to claim 25, further comprising using a splitter mirror to reflect light from the cylinder to the circuit structure along a direction from the first slit to the second slit.

27. A method according to claim 25, further comprising generating light in the cylinder using at least two light sources in the cylinder or the inner wall on mutually opposite sides of the virtual plane.

28. A method according to claim 27, further comprising reflecting light from the cylinder towards the first slit along the virtual plane from a surface part that receives light directly from at most a part of the light sources.

29. A method according to claim 28, further comprising adjusting an intensity of a light source in said part relative to the intensity of a further light source outside said part between inspection of different types of circuit structures.

30. A method according to claim 25, further comprising adjusting light emission properties of the light source to mutually different values for inspection of different substrates.

* * * * *